US009084395B2

(12) United States Patent
Vollmer et al.

(10) Patent No.: US 9,084,395 B2
(45) Date of Patent: Jul. 21, 2015

(54) METHOD TO ARREST GROWTH OF INVASIVE SPECIES' SEEDS WHILE IN NON-NATURAL ENVIRONMENT PRIOR TO TRANSPORT

(71) Applicants: Jennifer Vollmer, Greybull, WY (US); Sheilah Kennedy, Okanogan, WA (US)

(72) Inventors: Jennifer Vollmer, Greybull, WY (US); Sheilah Kennedy, Okanogan, WA (US)

( * ) Notice: Subject to any disclaimer, the term of this patent is extended or adjusted under 35 U.S.C. 154(b) by 266 days.

(21) Appl. No.: 13/677,106

(22) Filed: Nov. 14, 2012

(65) Prior Publication Data

US 2014/0130409 A1  May 15, 2014

(51) Int. Cl.
*A01G 1/00* (2006.01)
*A01N 57/20* (2006.01)

(52) U.S. Cl.
CPC ............... *A01G 1/001* (2013.01); *A01N 57/20* (2013.01)

(58) Field of Classification Search
CPC ............................... A01G 1/001; A01N 57/20
USPC ......................................... 504/206; 47/58.1 R
See application file for complete search history.

(56) References Cited

U.S. PATENT DOCUMENTS

2008/0305954 A1* 12/2008 Zawierucha et al. ......... 504/156

FOREIGN PATENT DOCUMENTS

CN         101796964 A    *  8/2010

OTHER PUBLICATIONS

Fleming, J., Vehicle Cleaning Technology for Controlling the Spread of Noxious Weeds and Invasive Species, 2005, United States Department of Agriculture, Forest Service, Technology & Development Program, pp. 1-36.*
Taylor, K., Washing Vehicles to Prevent Weed Seed Dispersal, 2011, MontGuide, Montana State University Extension, MT201106AG, pp. 1-4.*
Kennedy, S., Managing Invasive Species by Eliminating Vehicle Transfer, 2009, Invasive Plant Control, Strategic Management of Invasive Species in the Southeastern United States, pp. 1-31.*
Projects and How it Works. Website [online]. S-K Environmental Noxious Weed Wash, 2006 [retrieved on Sep. 25, 2014]. Retrieved from the Internet:<URLhttp://s-k-enviro.com/projects.html and http://s-k-enviro.com/how_it_works.html, 5 pages.*
Renz, M., Spotted Knapweed (*Centaurea* biebersteinnii), 2007, University of Wisconsin Weed-Factsheet, ,University of Wisconsin Extension, pp. 1-5.*

* cited by examiner

*Primary Examiner* — Sue Liu
*Assistant Examiner* — Andriae M Holt
(74) *Attorney, Agent, or Firm* — Peter J. Timbers; Walker & Studer, LLC

(57) ABSTRACT

This invention pertains to the application of a chemical composition rinse agent to equipment or vehicles and apparatuses generally used in non-agricultural areas in an effort to prevent the spread of undesired seeds of invasive species. The rinse agent comprises a composition known to inhibit growth of the mature variant of the invasive species. The application would be directly to equipment or vehicles or other mobile apparatuses.

12 Claims, 1 Drawing Sheet

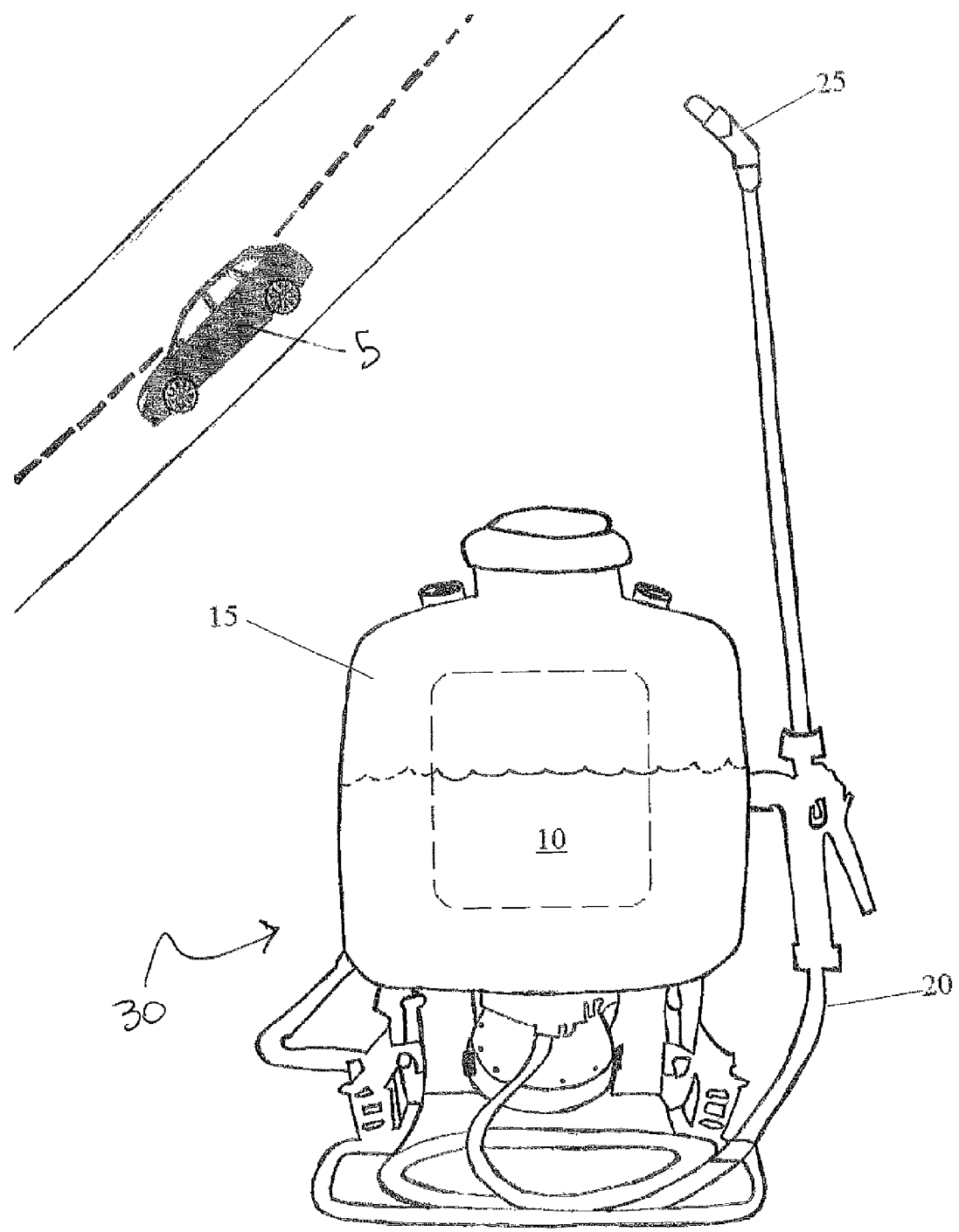

METHOD TO ARREST GROWTH OF INVASIVE SPECIES' SEEDS WHILE IN NON-NATURAL ENVIRONMENT PRIOR TO TRANSPORT

FIELD OF THE INVENTION

The invention pertains to the field of halting the spread of invasive species by arresting the growth of the seeds of invasive species when such seeds are attached to a vehicle of other transport apparatus. The method comprises a means for application and solution containing a tidal agent. Use of this method halts the spread of seeds of invasive species which are attached to an apparatus, a non-natural environment, prior to transport to a suitable growing environment.

BACKGROUND OF THE INVENTION

The spread of invasive species is a problem for those people who wish to see natural species protected and natural environments and ecosystems maintained. Invasive species often out-compete native species, permanently altering and destroying natural, native environments. Numerous governmental and nongovernmental entities are highly concerned about destruction of native species and ecosystems by invasive species.

Undesired seeds may become lodged on the undercarriage or other surfaces of a mobile apparatus, industrial and recreational. Water rinsings and water washings of the mobile apparatuses prior to transport is one method currently used to stop the spread of an invasive species from one locale contaminated with invasive species to locales that are not contaminated with invasive species.

Currently, no herbicide products, besides methyl bromide, are believed to have the ability to destroy seeds to the extent that they don't mature. Methyl bromide is a registered fumigant used for control of seeds in soil and soil sterilization. Use of methyl bromide is not preferred and restricted in many countries. The USDA and EPA funded 'fast track' programs for several years to discover replacement products for methyl bromide; however; similar replacements have yet to be found. Glyphosate inhibits the production of specific amino acids. Photosynthesis, transpiration and translocation must be occurring for the plant to produce amino acids. Other herbicides, such as contact herbicides (i.e. paraquat) cause free radicals in leaf cells, photosynthesis must be occurring for paraquat to cause free radicals. Hormone-type herbicides (i.e. 2,4-D) work by promoting or inhibiting growth hormones causing malformation or cell proliferation, interfering with the normal distribution of metabolites and nutrients for normal growth. Thus, herbicides are thought to exclusively function on actively growing plants or seedlings by affecting growth processes that are needed for these herbicides to work, according to current, conventional logic.

Herbicidal activity is thought to require active growth of a plant, such as photosynthesis, amino acid production, protein development, translocation of water, minerals and carbohydrates, or transpiration. Current knowledge shows no evidence that these processes are occurring in a dormant seed. Herbicides may be used for control of seeds in a soil environment, and are referred to as pre-emergent herbicides. They do not actually work by being absorbed through the seed coat to control the seed. The pre-emergent herbicides are loosely bound to soil collides and into moisture surrounding the soil. As the radical (root) and hypocotyl (stem, coleoptiles for grasses) emerge from the seed, they are exposed to moisture in the surrounding soil that contains the pre-emergent herbicide. The herbicide is absorbed by the seedling (not the seed) and growth is stopped, often prior to actual emergence from the soil.

Typically, a herbicide, such as glyphosate, binds very tightly to the soil and is not available for absorption by the hypocotyls or radical. In fact, the description from the Herbicide Handbook, Weed Science Society of America, $7^{th}$ Edition-1994 states that glyphosate is a nonselective and foliar-applied herbicide. The Handbook states that it can be used in pre-plant conditions at 0.21-2.24 kg ae/ha (0.88-2 lb ae/A) to control emerged weeds at planting in certain annual crops planted using no-till methods and post plant conditions at 0.84-4.2 kg ae/ha (0.75-3.75 lb ae/A) or at 0.5-5% v/v of a 360 g/L product in a spray-to-wet application for general vegetation control in many non-crop areas such as industrial sites. Further, a directed post-plant or site preparation at up to 4.2 kg/ae/ha in ornamentals and Christmas trees and directed post-plant at 0.84-4.2 kg ae/ha in tree and vine crops; pre-harvest at 0.84-4.2 kg ac/ha in cotton; pre-harvest at 0.21-0.84 kg ae/ha in wheat; post-plant at 0.16 kg ae/ha (0.14 lb ae/A) in bahia grass and Kentucky bluegrass, post-plant at 0.16-0.42 kg ae/ha in Bermuda grass, and post-plant at 21 kg ae/ha in fescue, orchard grass, and quack grass for suppression of these perennial grasses on orchard floors; and for control of woody vegetation by injection of frill treatment or by treating cut stumps. There is no mention of the herbicide being applied pre-emergence for weed seed control.

Other non-glyophosate herbicides, such as contact herbicides, are traditionally applied to above soil plant tissue, i.e., leaves and stems. These herbicides limit plant growth by creating free radicals or other type of cell damage. One of the reasons contact herbicides have not been considered for seed control is because soil interference prevents adequate herbicide coverage of the seed. Inadequate herbicide coverage of the seed due to soil interference is the major reason researchers have not considered traditional herbicides for killing seeds. There is no known research directed toward finding chemicals that will control seeds that are not in a soil type environment.

It is common practice that chemicals are used for disinfecting seeds prior to genetic manipulation. If these disinfectant products are used incorrectly or at too high of a dose, they can cause seed death. Further exploration into these products revealed that at high doses these disinfectants have a high toxicity to humans. General public use as a seed control product would therefore be precluded. While low toxicity products may enter the market at some time in the future, these products are not considered herbicides.

There is a need for a product to control invasive specie's seeds, when they are not in a soil environment. Invasive specie's seed control had not been necessary until studies and modeling of invasive species spread showed that travel corridors, such as roads and trails are the likely culprits with regard to introduction pathways for invasive species infestations. State Departments of transportation, forest services and parks, among others, are now concerned about the movement of noxious and invasive weeds from infested sites to pristine, non-contaminated sites.

Conventional and current wisdom believes that glyphosate is not used for control of seeds in a soil environment because glyphosate binds to the soil particles and is not available for absorption by germinating seedlings. Therefore, glyphosate is not used to control seeds in a conventional agricultural setting.

There is no conventional approach to controlling seeds and reproductive vegetation lodged or attached to equipment, vehicles or aquatic vessels, i.e., apparatuses. The only current available methods are fumigation and scalding hot water treatments. Such method is not acceptable for typical agricultural, non-crop or aquatic operations. Further, such methods used by non-professional individuals present safety concerns and many of the treatments are expensive due to the cost of treatment equipment. Additionally, the cost of heating water and difficulty providing the equipment needed for remote locations is often prohibitive. Pressure washing of the apparatuses can remove up to only 93% of the unwanted plant parts with soil debris. Thus, there is a long felt need for a system or method to eliminate the transportation of seeds and larvae from a contaminated locale to an uncontaminated locale.

SUMMARY OF THE INVENTION

Accordingly, it is an object of embodiments of the present invention to provide an invention which relates to a system and method to control the spread of seeds of invasive species. The invention relates to application of a chemical rinse agent to seeds of invasive species, prior to said seeds dislodging from an apparatus in a non-contaminated area.

The present invention is concerned with a new and novel use of rinse agents applied to seeds of invasive species when said seeds are in a non-natural environment. To achieve the foregoing and other objects, and in accordance with the purposes of the present invention, as embodied and broadly described herein, comprises a method to arrest growth of seeds of an invasive species attached to a mobile apparatus, said method comprising the following steps: preparing a liquid rinse agent, and applying said rinse agent to said mobile apparatus when the seed is in a non-natural environment. In one embodiment, the rinse agent comprises glyphosate.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

Benefits and advantages of the present invention include, but are not limited to, providing a method, which provides a means to arrest the growth of invasive species seeds in order to protect pristine or uncontaminated ecological systems or locales. The invention is easy to effectuate and can function in a variety of terrains without being cost prohibitive.

BRIEF DESCRIPTION OF THE DRAWINGS

The invention can be best understood by those having ordinary skill in the art by reference to the following detailed description when considered in conjunction with the accompanying drawings in which:

FIG. 1 illustrates a perspective view of one embodiment of the present invention showing the system means to apply liquid composition.

DETAILED DESCRIPTION OF THE INVENTION

Reference will now be made in detail to embodiments of the invention, examples of which are illustrated in the accompanying drawings. Throughout the following detailed description, the same reference characters refer to the same or similar elements in all figures.

FIG. 1 depicts one embodiment of the means to apply said rinse agent to a mobile apparatus 5. The spray equipment 30 comprising a nozzle portion 25, a reservoir portion 15 and a liquid transfer portion 20 in contact with both the nozzle portion 25 and the reservoir portion 15 such that the rinse agent 10 contained in the reservoir portion 15 can flow through the fluid transfer portion and out the nozzle via the fluid transfer portion and be applied to the mobile apparatus 5.

The step of applying the rinse agent to the mobile apparatus includes spraying the rinse agent to the outer surface and underneath surface of said mobile apparatus. It is further contemplated within the scope of this invention that the nozzle portion may be at a different electric potential than the mobile apparatus. Thus, there is an electrostatic mechanism for application of the rinse agent to allow for a uniform or even coating of the rinse along the surface of the apparatus. It has been found that a uniform coating of the rinse agent increases the efficiency of the system and method. During the application of the rinse agent, the undercarriage, sides and upper and lower surfaces of the mobile apparatus have a thorough application of the rinse agent.

While FIG. 1 depicts a mobile apparatus 5, which happens to be a depiction of an automobile, other examples of mobile apparatuses contemplated within the scope of this invention include any of the following: boat, wagon, truck, train, trailer, equipment, heavy equipment, transport device, recreational vehicle, motorcycle, and bicycle. As used in this invention apparatus refers to any object that transport in and out of a given local or environment to which seeds can attach and travel out of said locale or environment.

In terms of this invention, and as a means to distinguish between natural environments and non-natural environments, it is assumed that natural environment is any environment in which a seed of an invasive species could be expected to grow and mature, an example would include soil for seeds. In embodiments of this invention, the term non-natural environment includes roadways, streets, drives, parking areas, inspection areas, surfaces composed of metal, fiberglass, PVC, plastic, epoxy, rubber, glass, cement, asphalt, carpet, cloth, tarp and any area in which the seed cannot be expected to grow or mature. It is contemplated that within the scope of this invention that the metal, plastic or fiberglass outer surface of a mobile apparatus to which the seed of the invasive species is attached is a non-natural environment.

In embodiments of this invention, the term invasive species includes, but is not limited to, the following species: Russian knapweed, chouchun (tree of heaven), Persian silk tree (pink siris), garlic mustard, hedge garlic, coral bush, coralberry, giant reed, Spanish cane, Japanese barberry, Thunberg's barberry, downy brome, drooping brome, flowering rush, grass rush, musk thistle, nodding thistle, Australian pine, Filao tree, "killer algae", diffuse knapweed, white knapweed, spotted knapweed, yellow cockspur, yellow starthistle, camphor laurel, camphor tree, wild taro, Asiatic blue dayflower, poison hemlock, pampas grass, sulfur cosmos, yellow cosmos, dog-strangling vine, swallowwort, common broom, Scotch broom, air potato, Brazilian waterweed, large-flowered waterweed, common water hyacinth, Russian olive, Russian silverberry, autumn olive, Japanese silverberry, southern blue gum, Tasmanian blue gum, burning bush, winged euonymus, winter creeper vine, green spurge, leafy spurge, fleece flower, Japanese knotweed, common ivy, English ivy, giant cow parsley, giant hogweed, orange hawkweed, tawny hawkweed, Esthwaite waterweed, hydrilla, cogon, cogongrass, Chinese privet, European privet, wild privet, Japanese honeysuckle, Amur honeysuckle, Morrow's honeysuckle, Tartarian honeysuckle, Japanese climbing fern, Old World climbing fern, climbing maidenhair, creeping Jenny, herb twopence, moneywort, twopenny grass, purple loosestrife, purple lythrum, spiked loosestrife, broad-leaved paper bark, paper bark tea tree, niaouli, Natal grass, Natal redtop, rose Natal grass, bead tree, ceylon cedar, chinaberry, lunumidella, Persian lilac, white cedar, Japanese stiltgrass, Nepalese browntop, humble plant, shameful plant, sensitive plant, sleeping grass, touch-me-not, Eurasian water milfoil, Spiked water milfoil, cotton thistle, heraldic thistle, Scots thistle, Scottish thistle, woolly thistle, skunk vine, torpedo grass, parsnip, princess tree, Asiatic tearthumb, Chinese tearthumb, devil shield, devil's tail tearthumb, mile-a-minute weed, pink lady's thumb, common reed, curly-leaf pondweed, kudzu, baby rose, multiflora rose, rambler rose, Armenian blackberry, Himalayan blackberry, Japanese wineberry, wine raspberry, wineberry, curled dock, curly dock, narrow dock, sour dock, yellow dock, giant salvinia, kariba weed, aroeira, Brazilian pepper, Christmasberry, Florida holly, rose pepper, tropical soda apple, saltmarsh cordgrass, smooth cordgrass, Asiatic witchweed, saltcedar, tamarisk, water caltrop, water chestnut, Chinese tallow tree, Florida aspen, Gray popcorn tree, alligatorweed, Brazilian waterweed, caulerpa, Mediterranean clone, common reed, curly pondweed, didymo, Eurasian watermilfoil, giant reed, giant salvinia, hydrilla, melaleuca, purple loosestrife, water chestnut, water hyacinth, water lettuce, and water spinach.

In other embodiments of this invention, the term invasive species includes species declared noxious or invasive by law, or an alien (or non-natural) species whose introduction does, or is likely to cause economic or environmental harm or harm to human health.

This invention has been experimentally tested under several protocols and verified. Summary results are as follows:

All seeds for a Protocol 1 Test were removed from the flower parts and used as clean seeds. A treatment consisted of 100 seeds with four replications for a total of at least 400 seeds per treatment. In some cases extra seeds were treated to accommodate additional germination tests, if needed. In lots of 100, seeds were first rinsed with water to simulate a wash treatment. These pre-wetted seeds were then dipped for one minute in one of the Treatment Rinse percent solutions per volume as show below. Three quality glyphosate products were used. Treatments 3 through 6 were the same glyphosate product, meaning they contained the same make-up of inert ingredients (Inerts). The inert ingredients typically comprise tallow amine, lecithin, algaecide and purified water. Treatment 2 inert ingredients did not contain tallow amine. The surfactants added to the percent solution were a penetrator, comprising methylated seed oil, and a spreader, comprising polyether-polymethylsiloxane-copolymer polyether or silicone polyether copolymer. Treatments 5 and 6 did not contain the spreader surfactant.

TABLE 1

Treatment Rinse percent solutions per volume

| Treatment | % Glyphosate | % Inerts | % Surfactant |
|---|---|---|---|
| 1 | 9.7 | 10.3 | 2% |
| 2 | 10 | 9.4 | 2% |
| 3 | 11.3 | 16.2 | 2% |
| 4 | 6.15 | 8.85 | 2% |
| 5 | 11.3 | 16.2 | 1% |
| 6 | 6.15 | 8.85 | 1% |

Seeds were stirred during the dip to assure all seeds were exposed to the solution. Treated seeds were allowed to air dry with the time to dry recorded. Three main seed types were used in the Protocol 1 Test: whitetop (*Cardaria draba*), spotted knapweed (*Centauria maculosa*), and diffuse knapweed (*Centauria. diffusa*). Two additional seed types were used for one treatment each, Russian thistle (*Salsola tragus*) and Scotch thistle (*Onopordum acanthium*).

When seeds were thoroughly dry after treatment they were packaged and sent for germination testing. Each treatment of four replications had an associated non-treated replication of 100 seeds, for a total of at least 400 non-treated seeds per treatment. Non-treated seeds received only the initial rinse treatment of water. After thoroughly drying they were packaged and sent for germination testing the same as the treated seed. Germination tests were typically started within two to three weeks after treatment. Scotch thistle germination tests were delayed longer due to a dormancy characteristic of the seed.

The intact flower test procedure included three main seed types: whitetop, spotted and diffuse knapweed, which were utilized in a Protocol 2 Test. Seeds were left in the flower heads or seed capsules during treatment. The number of seeds per flower head or capsule was estimated and enough material was used in testing to give an equivalent number of seeds to Protocol 1, 100 seeds per replication, with four replications, plus the associated non-treated control lot. Treatment was conducted by spreading out the material on a clean mat, spraying with water until wet to simulate the wash treatment of the system, followed by, while still wet, an application of treatment one or two listed in Table 1. Treatments were applied at approximately 20 gallons per acre utilizing a hand wand with a typical flat fan nozzle. The control material received only the initial water treatment, sprayed until wet. The intact wetted and treated material was allowed to thoroughly dry, packaged and sent for germination testing.

Overall results indicate glyphosate greatly reduced the survivability of the treated weed seed independent of which inert ingredients or surfactant was incorporated in the percent solution because the growth of treated seeds was abnormal. The direction of growth of the radical (root) was up and the hypocotyl (shoot) was down, opposite to the growth of the normal seeds of the control. When germinated, treated seeds never formed root hairs or secondary roots. The radical typically rotted off by 14 days after germination. The seedlings from treated seeds were weak and never grew past the cotolydon stage when grown in green house soil. This growth pattern would not be sustainable in a natural environment.

Clean seed treatment results for whitetop indicate that there was a 100% control with no normal growth occurring from treated seeds, for all treatments. Additionally, there was no substantial or consistent change in the number of not germinated or dead seeds between the treated and control seeds. There was no noticeable difference between treatments, 3 verses 5 and 4 versus 6, when the spreader additive was removed from the treatment solution.

Spotted and diffuse knapweed both showed a consistent increase in the number of not germinated seeds resulting from the treatments. On the average, there was a fivefold increase in not germinated seeds for treated compared to control seed lots. The spotted knapweed appeared to be more sensitive to the treatments than the diffuse knapweed. All glyphosate treatments that included tallow amine stopped normal growth of spotted knapweed seeds except for 2% (2 out of 100 seeds) normal germination in treatment 6, the treatment with the lowest glyphosate rate and no spreader. A comparison of treatments 3 versus 5 and 4 versus 6, shows that the number of seeds that exhibited abnormal growth decreased while the number of non-germinated seeds increased; however; the overall result on seed control was unchanged.

Control results for diffuse knapweed showed a similar but more exaggerated result trend compared to the spotted knapweed results. The biggest difference for diffuse knapweed, when compared to both the whitetop and spotted knapweed, was that a small percent of treated diffuse knapweed seeds exhibited normal growth. Treatment 2 had the greatest number of normal growing seeds, 22%. The remaining treatments had normal growth that ranged from 6% to 8%. The only exception was treatment 5, where the high rate of glyphosate with tallow amine and no spreader had 0% normal growth.

Russian thistle was only treated with treatment 2 which did not contain tallow amine. Russian thistle is one weed that is wide spread and although it is invasive it is not listed as noxious in any state. Russian thistle seeds are actually germinated in the seed coat, allowing the plant to start growth early in the season and in drought situations, when other weed germination will be delayed or non-existent. Additionally, this plant readily becomes resistant to herbicides, indicating it may have highly diverse genetics. The growth stage of the embryo and diverse genetics may explain the response of necrotic growth in some seeds in addition to the normal growth and abnormal growth similar to the other species. Overall, results were just below acceptable with 22% normal growth. However, the other species already illustrated that the treatment without tallow amine provides less control.

Due to the dormancy mechanism of Scotch thistle, germination tests had to be done in a soil environment instead of a growth chamber. Initial results showed a lower rate of treated seeds germinated, and no treated seeds resulted in a plant that matured beyond the cotyledon stage, similar to the other weed types tested. The non-treated control seeds produced healthy plants that matured in to the expected rosette. The scotch thistle soil test proves that there is a difference between treating the seed directly and treating the soil in which the seed exists. Scotch thistle is not controlled with a soil application of glyphosate; however, it was controlled with a direct application of glyphosate to the seed, then placed in soil to germinate. Whitetop, spotted knapweed and diffuse knapweed germination tests conducted in soil flats confirmed the Scotch thistle results, with no treated seeds showing the ability to become mature plants.

Intact flower treatment results indicate that overall the number of non-germinated seeds increased over the clean seed tests in both the treated and control seed lots. There was no consistent trend between the treatments of glyphosate with tallow amine as one of the inert ingredients versus the glyphosate without tallow amine, Treatment 2. All treatments achieved an acceptable amount of control with only 0% to 8% normal growth.

Results indicate that, when summarizing results from all species, there was no substantial difference between treatments except a slight decrease in control (abnormal growth+ non-germinated seeds) when tallow amine was not included in the treatment. However; this claim was not substantiated with the trials of the intact flowers. Results with Treatment 2 were still well within the acceptable goals of the study. The rate decrease and the removal of the spreader did not show a consistent decrease in over all control, suggesting that the threshold rate of glyphosate had not been reached in these studies. Overall the results show excellent success at stopping seed growth with the herbicidal products researched.

Overall results showed that a traditionally foliar applied herbicide can be used to control seeds in a non-soil environment. When considering treated seeds that may grow to reproductive maturity, glyphosate treatments can achieve 95% control of whitetop, 100% control of spotted knapweed, 99% control of diffuse knapweed, 100% control of Scotch thistle and 72% control of Russian thistle. These results are unexpected because glyphosate manufacturers and distributors have never claimed or warned of damage to seeds that would be directly exposed to a glyphosate application, such as, desirable seeds that lay on the top of the soil or seeds in planting furrows that are not covered with soil. It is reasonable to expect that other herbicidal products that do not warn of seed injury, in combination with quality additives, may also hinder seed germination or growth if applied in a non-soil environment with penetrating additives, due to the higher level of exposure the seed and seed embryo may have to the herbicide.

The fact that glyphosate works to control seeds is unexpected given current understanding of glyphosate mechanisms. Seeds have a protective outer layer, the episperm, which is unlike other plant material. The episperm of seeds is often a testae, which is a thick or hard outer coat which has long been considered too difficult for herbicides to penetrate. Other than fumigants, herbicides that are soil applied for weed seed control, are absorbed from the soil moisture by the radical or hypocotyle. Herbicides are not known to be adsorped or absorbed by the testae in sufficient quantity to result in arresting growth of a seed. When used within the EPA approved label rates, glyphosate is not absorbed by the radical or hypocotyls because it is strongly adsorbed to the soil particles, having a $K_{ow}$ of 0.0006-0.0017. Thus, the surprising result is that glyphosate can function to render invasive species' seeds ineffective to mature into foliating plants, thereby stopping the spread of invasive species.

When seeds are in a non-soil environment they often are attached to an apparatus. They may be typically lodged under a vehicle frame or on farm equipment that has been power washed. In such circumstance, an application of a rinse agent containing glyphosate will allow glyphosate to adsorb and/or absorb to seeds and reproductive vegetative parts. When the seed or vegetative part becomes dislodged from the equipment and drops in a suitable growing condition, the adsorbed and/or absorbed glyphosate interferes with normal plant growth, preventing establishment.

In addition to glyphosate, other known compositions comprise chemicals have the same potential to be effective to destroy the ability of seeds to grow into maturity when used in the same manner, as described above. In the present invention, compositions include, but are not limited to, imidazolinones, sulfonylureas, dinitroanilines, phenoxys, benzoic acids, bipyridiliums, triazines, ammonia, acid, chorine-containing compounds, chlorine dioxide, pyridinecarboxylic acids, benzonitriles, fluridone, endothall, indaziflam, aminocyclopyrachlor, triisopropanolammonium, and variants and derivatives of above.

In one embodiment, the liquid composition comprises any of the following additives: inert ingredients, surfactants, adjuvant agents, spreaders, stickers, penetrants, buffering agents, water treatments, drift control agents, wetting agents, foaming agents, defoaming agents, water, purified water, gasoline, diesel oil, ethylated seed oil, methylated seed oil, silicone based surfactants, crop oil concentrates, tallow amines, lecithin, algaecide, silicones, polyether-polymethylsiloxane-copolymer polyether, silicone polyether copolymer and nonionic surfactants.

In one embodiment of the present invention, the method further comprises the step of pressurization of the rinse agent. It is also contemplated within the scope of the invention that the pressurization is accomplished by any of the following means: addition of carbon dioxide, electric pumping, pneumatic pumping, gas pumping.

It is further contemplated within the scope of this invention that the system and method includes a water-composition wash to clean seeds of invasive species of plant, dust, aquatic or animal matter attached or in contact with the seed. With regard to the method embodiment of the present invention, method comprises an additional step of applying a water-composition prior to the rinse agent. In one embodiment of the present invention, the water-composition wash is a high pressure wash. In another embodiment of the present invention, the system includes an additional reservoir portion comprising a water-composition to provide a pre-rinse agent wash.

Through the use of this invention, seeds of invasive species can be halted in a safe and inexpensive manner. It is believed that the apparatus of the present invention and many of its attendant advantages will be understood from the foregoing description. It is also believed that it will be apparent that various changes may be made in the form, construction, and arrangement of the components without departing from the scope and spirit of the invention and without sacrificing its material advantages. The forms described are merely exemplary and explanatory embodiments thereof. It is the intention of the following claims to encompass and include such changes.

What is claimed is:

1. A method to arrest growth of seeds of an invasive species attached to a mobile apparatus, said method comprising the following steps: preparing a liquid rinse agent, and applying said rinse agent to said mobile apparatus when the seed is in a non-natural environment, wherein said rinse agent comprises a herbicide.

2. The method of claim 1, wherein the rinse agent comprises glyphosate.

3. The method of claim 1, wherein the rinse agent is selected from the group of compounds consisting of imidazolinone herbicides, sulfonylurea herbicides, dinitroaniline herbicides, phenoxy herbicides, benzoic acid herbicides, bipyridilium herbicides, triazine herbicides, pyridinecarboxylic acid herbicides, benzonitrile herbicides, fluoridine, endothall, indaziflam, aminocyclopyrachlor and derivatives thereof.

4. The method of claim 1, wherein the rinse agent further comprises additives selected from the group consisting of inert ingredients, surfactants, adjuvant agents, spreaders, stickers, penetrants, buffering agents, water treatments, drift control agents, wetting agents, foaming agents, defoaming agents, water, purified water, gasoline, diesel oil, ethylated seed oil, methylated seed oil, silicone based surfactants, crop oil concentrates, tallow amines, lecithin, algaecide silicone, polyether-polymethylsiloxane-copolymer polyether, silicone polyether copolymer and non-ionic surfactants.

5. The method of claim 1, wherein the method further comprises the step of pressurization of the rinse agent prior to the step of applying the rinse agent to said mobile apparatus.

6. The method of claim 5, wherein the pressurization of the rinse agent is selected from the group consisting of addition of carbon dioxide, electric pumping, pneumatic pumping, and gas pumping.

7. The method of claim 1 further comprising the step of applying the liquid rinse agent via electrostatic spraying via a differential electrical potential between the mobile apparatus and the means to apply said liquid rinse agent.

8. The method of claim 1, wherein the non-natural environment is selected from the group consisting of roadways, streets, drives, parking areas, inspection areas, surfaces composed of metal, fiberglass, PVC, plastic, epoxy, rubber, glass, cement, asphalt, carpet, cloth, tarp and any area in which the seed cannot be expected to grow or mature.

9. The method of claim 1, wherein the invasive species is selected from the group consisting of Russian knapweed, chouchun (tree of heaven), Persian silk tree (pink siris), garlic mustard, hedge garlic, coral bush, coralberry, giant reed, Spanish cane, Japanese barberry, Thunberg's barberry, downy brome, drooping brome, flowering rush, grass rush, musk thistle, nodding thistle, Australian pine, Filao tree, killer algae, diffuse knapweed, white knapweed, spotted knapweed, yellow cockspur, yellow starthistle, camphor laurel, camphor tree, wild taro, Asiatic blue dayflower, poison hemlock, pampas grass, sulfur cosmos, yellow cosmos, dog-strangling vine, swallowwort, common broom, Scotch broom, air potato, Brazilian waterweed, large-flowered waterweed, common water hyacinth, Russian olive, Russian silverberry, autumn olive, Japanese silverberry, Tasmanian blue gum, burning bush, winged euonymus, winter creeper vine, leafy spurge, fleece flower, Japanese knotweed, common ivy, English ivy, giant cow parsley, giant hogweed, orange hawkweed, Esthwaite waterweed, hydrilla, cogon, cogongrass, Chinese privet, European privet, wild privet, Japanese honeysuckle, Amur honeysuckle, Morrow's honeysuckle, Tartarian honeysuckle, Japanese climbing fern, Old World climbing fern, climbing maidenhair, creeping Jenny, purple loosestrife, broad-leaved paper bark, Natal grass, bead tree, ceylon cedar, chinaberry, lunumidella, Persian lilac, white cedar, Japanese stiltgrass, Nepalese browntop, humble plant, shameful plant, Eurasian water milfoil, Spiked water milfoil, Scottish thistle, skunk vine, torpedo grass, parsnip, princess tree, Asiatic tearthumb, devil shield, pink lady's thumb, common reed, curly-leaf pondweed, kudzu, baby rose, multiflora rose, rambler rose, Armenian blackberry, Japanese wineberry, curly dock, narrow dock, sour dock, yellow dock, giant salvinia, aroeira, Brazilian pepper, Christmasberry, Florida holly, rose pepper, tropical soda apple, saltmarsh cordgrass, smooth cordgrass, Asiatic witchweed, saltcedar, water caltrop, Chinese tallow tree, alligatorweed, Brazilian waterweed, caulerpa, Mediterranean clone, didymo, Eurasian watermilfoil, melaleuca, water chestnut, water lettuce, and water spinach.

10. The method of claim 1, wherein the invasive species is is selected from the group consisting of species declared noxious or invasive by law and an alien (or non-natural) species whose introduction does, or causes economic or environmental harm or harm to human health.

11. The method of claim 1, wherein method comprises an additional step of applying a water-composition prior to applying the rinse agent.

12. The method of claim 1, wherein the step of applying said rinse agent to said mobile apparatus includes spraying the rinse agent to the outer surface and underneath surface of said mobile apparatus.

* * * * *